(12) United States Patent
Wei et al.

(10) Patent No.: US 6,577,384 B2
(45) Date of Patent: Jun. 10, 2003

(54) SPATIAL AVERAGING TECHNIQUE FOR ELLIPSOMETRY AND REFLECTOMETRY

(75) Inventors: Lanhua Wei, Fremont, CA (US); Hanyou Chu, Santa Clara, CA (US); Jon Opsal, Livermore, CA (US)

(73) Assignee: Therma-Wave, Inc., Fremont, CA (US)

( * ) Notice: Subject to any disclaimer, the term of this patent is extended or adjusted under 35 U.S.C. 154(b) by 0 days.

(21) Appl. No.: 09/871,220

(22) Filed: May 31, 2001

(65) Prior Publication Data

US 2002/0012123 A1 Jan. 31, 2002

Related U.S. Application Data

(62) Division of application No. 09/658,812, filed on Sep. 11, 2000, now Pat. No. 6,281,027.
(60) Provisional application No. 60/153,932, filed on Sep. 15, 1999.

(51) Int. Cl.[7] .................... G01N 21/00; G01N 21/55; G01J 4/00
(52) U.S. Cl. ................. 356/73; 356/369; 356/445
(58) Field of Search ................. 356/364, 369, 356/445, 630, 73

(56) References Cited

U.S. PATENT DOCUMENTS

| | | | |
|---|---|---|---|
| 4,955,062 A | | 9/1990 | Terui .................. 382/8 |
| 5,159,412 A | * | 10/1992 | Willenborg et al. ... 250/559.07 |
| 5,840,595 A | | 11/1998 | Kobayashi ............ 438/16 |
| 6,160,826 A | | 12/2000 | Swanson et al. ...... 372/20 |
| 6,172,752 B1 | | 1/2001 | Haruna et al. ........ 356/357 |
| 6,191,855 B1 | | 2/2001 | Maris ................. 356/357 |
| 6,201,608 B1 | | 3/2001 | Mandella et al. ..... 356/491 |

OTHER PUBLICATIONS

J.T. Fanton et al., "Multiparameter measurements of thin films using beam–profile reflectometry," *J. Appl. Phys.*, vol. 73, No. 11, Jun. 1, 1993, pp. 7035–7040.

J.M. Leng et al., "Simultaneous measurements of six layers in silicon on insulator film stack using spectrophotometry and beam profile reflectometry," *J. Appl. Phys.*, vol. 81, No. 8, Apr. 15, 1997, pp. 3570–3578.

* cited by examiner

Primary Examiner—Zandra V. Smith
(74) Attorney, Agent, or Firm—Stallman & Pollock LLP

(57) ABSTRACT

This invention relates to optical metrology tools that are used to evaluate small measurement areas on a semiconductor wafer, where the measurement area is surrounded by a material different from the measurement area. In one embodiment, a probe beam is scanned over the measurement area and the surrounding material as data is taken at multiple locations. A processor determines the characteristics of the measurement area by identifying an extremum value of the measurements which represents the center of the measurement area. In another embodiment, the processor determines the characteristics of the sample using a combination of light measured from within and without the measurement area. The measured data is treated as a combination of light from both regions and mathematically modeled to account for both the contribution of the light reflected from the measurement area and the light reflected from the surrounding material.

8 Claims, 3 Drawing Sheets

SPATIAL AVERAGING TECHNIQUE FOR ELLIPSOMETRY AND REFLECTOMETRY

This application is a divisional of application Ser. No. 09/658,812, filed Sep. 11, 2000, now U.S. Pat. No. 6,281,027, which claims the benefit of provisional application serial No. 60/153,932, filed Sep. 15, 1999.

FIELD OF THE INVENTION

This invention relates to ellipsometry and reflectometry optical metrology tools that are used to evaluate semiconductor wafers and is directed to reducing errors associated with material surrounding a desired measurement area or pad, either by minimizing the uncertainties in positioning the measurement beam or by taking into account the effects of the surrounding material in analyzing the measured data.

BACKGROUND OF THE INVENTION

As captured by Moore's Law, there is a longstanding trend in the semiconductor industry toward higher device densities and correspondingly smaller device geometries. The ellipsometry and reflectometry optical metrology tools that are used to evaluate semiconductor wafers must be able to respond to these ever decreasing device geometries by making measurements within smaller and smaller areas. Accordingly, a problematic circumstance has now arisen such that the size of the desired measurement area or measurement "pad" is comparable to the size of the optical spot used to make the measurement. An example of this circumstance is illustrated in FIG. 1. When this circumstance occurs, the measurement of the pad can be influenced by light reflected from the surrounding material. This influence in turn corrupts the accuracy and repeatability of the measurement because the surrounding material has different optical properties and a different depth than does the measurement pad itself.

In the case of the FIG. 1 example, the desired measurement would be of the thin layer 10 at the bottom of the well. The thin film layer 10 might be composed of a thin gate oxide layer, for instance. Crowding the beam is a top layer 20 that could well be composed of an entirely different material with significantly different optical properties than the layer to be evaluated.

In order to effectively apply optical metrology to semiconductor wafers, it is extremely important to be able make measurements with great precision and accuracy. For example, it is not uncommon to require layer thickness measurements to be repeatable to less than 0.1 Å (1/30$^{th}$ of an oxide monolayer). Such very high precision requires that the nature of the reflected light be known with corresponding precision.

When the spot size of the measurement beam approaches the size of the measurement pad, accurate positioning of the sample becomes especially critical. Typical sample stages used in metrology tools have positioning uncertainties on the order of a few microns, largely as a result of backlash in the mechanical linkages of the stage or drive mechanism. A few microns can constitute a significant percentage of the dimensions of the measurement pad. Thus, in order to reliably localize the optical spot of the measurement beam entirely within the pad to be evaluated, one needs to either reduce the size of the optical spot, or to take steps to somehow get around the stage inaccuracy. Although pattern recognition systems (in which the sample image is compared to a stored image of the target area) can reduce the positioning uncertainty somewhat, the physical limitations of the stage hardware are always present at some level.

It also bears noting that even if the optical spot appears to be small in terms of the usual definitions of spot size (e.g., the 1/e$^2$ beam width or Gaussian radius), there are often very faint tails that can extend well beyond these definitions. Given the extreme sensitivities required to accurately measure the thicknesses of very thin films, these very faint effects can cause an unacceptably large error. For example, we have found that for a Gaussian beam (typical of a well-focused laser) faint tails extending out to 3 times the Gaussian radius will corrupt the signals to an unacceptable degree. While it may be possible to "flatten" the beam profile to minimize the presence of such faint Gaussian tails using an aperture or other diffractive element, such techniques would tend to create undesirable interference fringes along the optical path within the instrument.

In fact, although shrinking the optical measurement spot size may generally be desirable in itself, such shrinking always comes at some cost. If the measurement beam source has a broad spatial extent (such as a tungsten filament or the arc of an arc lamp), then the light intensity at the sample surface tends to have an upper limit such that shrinking the optical spot means lowering the total amount of light. In turn, lowering the total light available for measuring tends to degrade the performance characteristics of the instrument because of decreased signal to noise ratios. Even if the measurement beam is bright and well collimated (such as a laser beam), the optical spot size will be still be limited by the power and complexity of the focusing lenses used to focus the beam on the sample surface. For a given beam diameter, shrinking the spot size means decreasing the focal length of the focusing lenses. This means crowding the lenses closer to the sample which, for off-axis optical systems, is a major inconvenience. This is so because typically one eventually runs into either the sample or some other optic used in the tool (e.g., a normal incidence lens used for a pattern recognition system). In addition, these high-numerical aperture lenses tend to be more prone to aberrations, and the larger curvatures can adversely impact the sensitive optical phase measurements needed for ellipsometry.

Once the practical limit for the optical spot size is reached, the only ways to minimize the effects of the surrounding material are either to somehow reduce the uncertainties in stage positioning or else to take into account the surrounding material in the analysis of the measured data. One aspect of the present invention is directed to a means of minimizing the stage positioning uncertainties by using a novel technique for finding the center of the measurement pad. This technique takes advantage of the fact that while the absolute accuracy of a positioning stage may be as poor as several microns, the ability of the stage to make incremental movements is much finer. In another aspect, the present invention is directed to a novel method for taking into account the effects of the surrounding material in analyzing the measured data.

SUMMARY OF THE INVENTION

It is an object of the present invention to remove errors created by material surrounding a measurement pad, either by reducing the uncertainties in stage positioning or by taking into account the surrounding material in analyzing the measured data.

In a first aspect of the present invention utilizes a technique where initially one purposefully aims to place the optical spot of the measurement beam a few microns away from the center of-the target pad. Then a series of measurements are made with each measurement separated by a small stage jog as the optical spot is scanned over the measurement pad. The data from these measurements are stored for analysis at the end of the scan. Once the scan is complete, these data are analyzed to find the center of the pad. Provided the surrounding material is the same on both sides of the pad (nearly always the case), one finds that some aspect of the data invariably has either a cup or inverted "U" shape or an inverted cup or "U" shape when viewed as a function of position. This cup or U-shape simply reflects the fact that the surrounding material is altering the measurement and that the perturbation of the data is a minimum at the center of the pad. The point of minimum perturbation should correspond to a minimum in the slope of the curve. Once this minimum is identified, the position along the wafer corresponding to that data point is selected as representing the center of the pad.

In another aspect of the present invention, a novel method of data analysis is used that allows for the correction of the effects of the surrounding material in analyzing the data. In essence, the data collected at the center of the pad is treated as being created by a superposition of light coming from the pad material itself and light coming from the surrounding material. The influence of the two materials is weighted by the proportion of the light that reflects off the pad as compared with the light that reflects off of the surrounding material. Given knowledge of both the dimensions of the pad and the size and profile of the beam spot, the resulting signal may be mathematically modeled to account for both the contribution of the light reflected from the pad and the light reflected from the surrounding material.

DETAILED DESCRIPTION OF THE INVENTION

More specifically, the first aspect of the present invention utilizes a technique where initially one purposefully aims to place the optical spot of the measurement beam a few microns away from the center of the target pad. Then a series of measurements are made with each measurement separated by a small stage jog as the optical spot is scanned over the measurement pad. The data from these measurements are stored for analysis at the end of the scan. Once the scan is complete, these data are analyzed to find the center of the pad. Provided the surrounding material is the same on both sides of the pad (nearly always the case), one finds that some aspect of the data invariably has either a cup or inverted "U" shape or an inverted cup or "U" shape when viewed as a function of position. This cup or U-shape simply reflects the fact that the surrounding material is altering the measurement and that the perturbation of the data is a minimum at the center of the pad. The point of minimum perturbation should correspond to a minimum in the slope of the curve. Once this minimum is identified, the position along the wafer corresponding to that data point is selected as representing the center of the pad.

Note that if the pad is wide enough then there may actually be several consecutive points which show no perturbation from the surrounding material. For pads that are roughly comparable in size to the optical spot, however, there may be one best location.

Although in most cases the most efficient scanning method is to scan the measurement pad across the focus, other scanning patterns may be employed to practice the present invention so long as the resulting data includes data points that correspond to measurements made at or near the center of the measurement pad. Scanning can also be made along two axes or directions rather than one.

Figure 2:
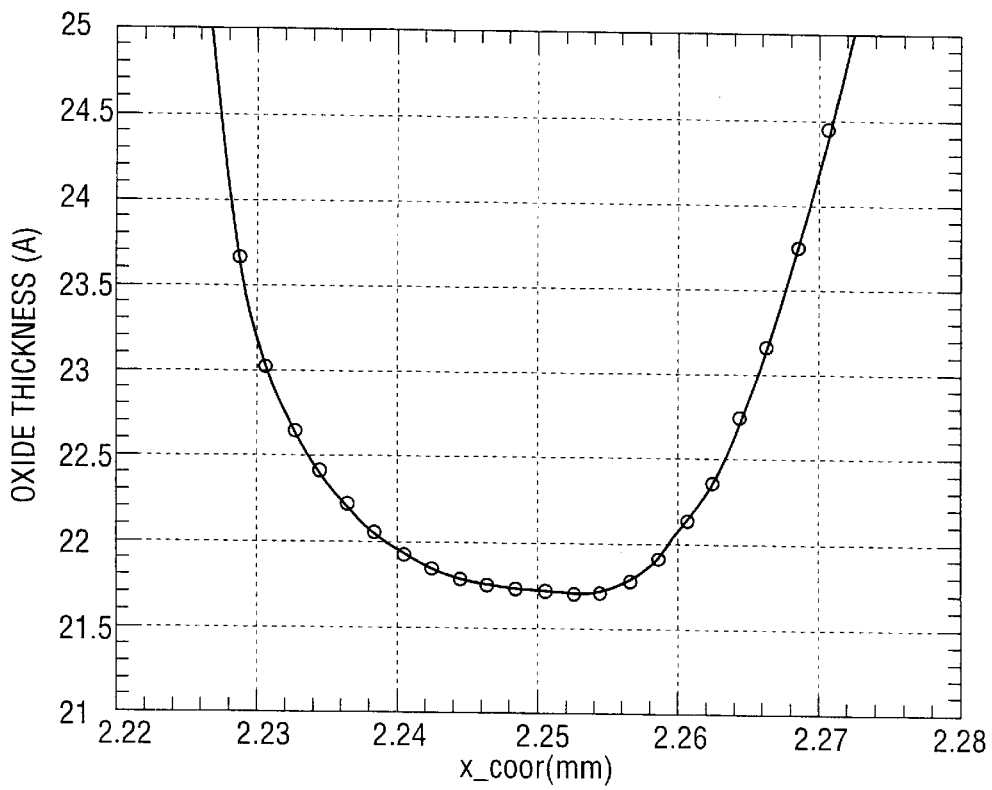
FIG. 2 shows an example of the graph of a linescan measurement made according to a method of the present invention.
Figure 3:
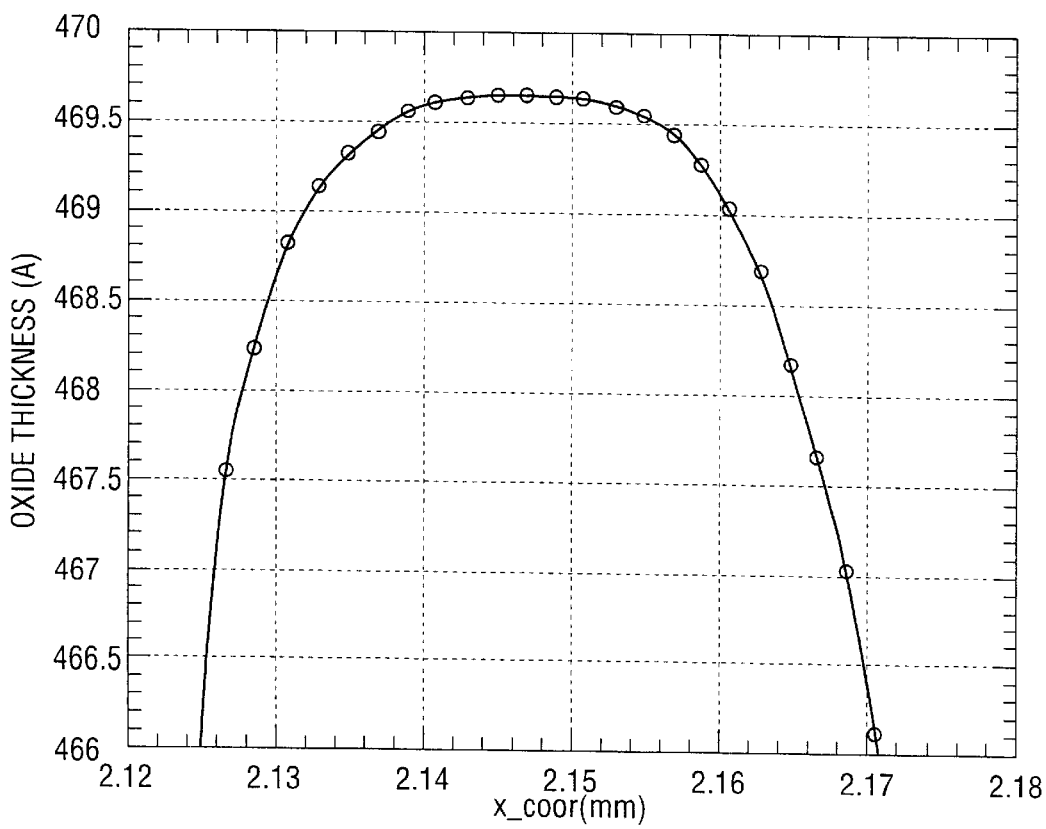
FIG. 3 shows a second example of the graph of a linescan measurement made according to a method of the present invention.

FIGS. 2 and 3 illustrate examples of graphs formed by purposefully making a linescan of measurements over the true center of the measurement pad. One preferred approach to making such measurements includes the use of the OPTIPROBE detector manufactured and sold by Therma-Wave, Inc. of Fremont, Calif., assignee herein, and described in part in one or more of the following U.S. Pat. Nos.: 4,999,014; 5,042,951; 5,181,080; 5,412,473; and PCT publication WO 99/02970, each of which is incorporated herein by reference in its entirety. The OPTIPROBE detector is capable of making both reflectometric and ellipsometric measurements.

In FIGS. 2 and 3, the range or Y-axis of the graphs shows the apparent layer thickness in angstroms for each measurement point if calculated without taking into account the perturbation of the material surrounding the measurement pad, while the abscissa or X-axis shows the position along the wafer in mm. In practice the layer thickness calculations for each measurement point can be made from the reflectometry or ellipsometry data using an appropriate iterative nonlinear least squares optimization technique such as the well-known Marquardt-Levenberg algorithm. The reason for resorting to a calculational least squares algorithm is that the Fresnel equations that describe the reflectometric and ellipsometric phenomena being measured are not easily inverted. A suitable iterative optimization technique for this purpose is described in "Multiparameter Measurements of Thin Films Using Beam-Profile Reflectivity," Fanton et al., Journal of Applied Physics, Vol. 73, No. 11. p.7035 (1993) and "Simultaneous Measurement of Six Layers in a Silicon on Insulator Film Stack Using Spectrophotometry and Beam Profile Reflectometry," Leng et al., Journal of Applied Physics, Vol. 81, No. 8, p.3570 (1997). These two articles are hereby incorporated by reference in their entireties.

When such appropriate calculational techniques were used to find a film thickness value for the series of measurements shown in FIG. 2, the result for the thin film being measured was a cup or U-shape, indicating that the material surrounding the measurement pad perturbed the apparent film thickness upward in value. This upward perturbation reflects the fact that in the FIG. 2 example, the surrounding material was higher than the thin film being measured. In this case, the 100 micron by 100 micron measurement pad was in the form of a well or depression. In the FIG. 2 graph, the point of minimum perturbation appears to occur generally between the position of 2.25 mm and the position of 2.254 mm.

For the FIG. 3 graph, the result is an inverted U-shape for the graph, indicating that the material surrounding the measurement pad perturbed the data so as to lower the apparent value of the film thickness. This downward perturbation reflects the fact that in the FIG. 2 example, the surrounding material was lower than the thin film being measured. In this case, the 100 micron by 100 micron measurement pad was in the form of a plateau or raised surface. In the FIG. 3 graph, the point of minimum perturbation appears to fall generally between the position of 2.142 mm and 2.15 mm.

The advantages of the present method can be seen from the data compiled in Tables 1 and 2 below. The data in Tables 1 and 2 were generated by measuring the thickness of a thin film on a test wafer. The wafer was measured at five points (sites) during each run. The five sites are identified in the Table as "T"(top), "C" (center), "B" (bottom), "L" (left), "R" (right). The measurements in Table 1 were made by moving the wafer to each site using a conventional high precision stage and a site correcting pattern recognition system. The measurements in Table 2 were taken using the site correcting pattern recognition system in conjunction with the linescan approach described herein. In particular, the wafer was brought to a spot which was thought to be slightly removed from the desired measurement site. Measurements were then taken across a 40 micron scan. Data were selected by identifying the minimum perturbation point of each scan. The measurement data of each run of Table 2 were taken immediately after the correspondingly numbered run of Table 1. The 15 different runs were spread out over five days to check repeatability.

TABLE 1

Jobfile: 5P_AE3 (No linescan)

| Site\Run | T | C | B | L | R | Mean/Waf |
|---|---|---|---|---|---|---|
| 1 | 108.15 | 107.66 | 108.05 | 107.78 | 107.23 | 107.77 |
| 2 | 107.16 | 106.07 | 106.00 | 106.35 | 105.96 | 106.31 |
| 3 | 107.14 | 106.24 | 106.00 | 106.27 | 105.96 | 106.32 |
| 4 | 107.12 | 106.09 | 106.00 | 106.25 | 105.96 | 106.28 |
| 5 | 107.36 | 106.09 | 106.14 | 106.38 | 105.99 | 106.39 |
| 6 | 107.14 | 106.17 | 106.10 | 106.46 | 105.97 | 106.37 |
| 7 | 107.39 | 106.39 | 106.10 | 106.27 | 105.96 | 106.42 |
| 8 | 107.08 | 106.11 | 106.04 | 106.27 | 106.02 | 106.30 |
| 9 | 107.26 | 106.14 | 106.04 | 106.42 | 105.98 | 106.37 |
| 10 | 107.16 | 106.17 | 106.10 | 106.37 | 106.00 | 106.36 |
| 11 | 107.46 | 106.20 | 106.11 | 106.48 | 106.04 | 106.46 |
| 12 | 107.32 | 106.31 | 106.19 | 106.30 | 106.17 | 106.46 |
| 13 | 107.72 | 106.31 | 107.09 | 106.85 | 106.65 | 106.92 |
| 14 | 107.11 | 106.26 | 106.08 | 106.34 | 106.41 | 106.44 |
| 15 | 108.51 | 106.14 | 106.26 | 106.45 | 106.08 | 106.69 |
| Mean | 107.41 | 106.29 | 106.29 | 106.48 | 106.16 | 106.52 |
| Sigma | 0.40 | 0.38 | 0.54 | 0.37 | 0.34 | 0.37 |

TABLE 2

Jobfile: 5P_40 (40 um linescan, 2 m/pt)

| Site\Run | T | C | B | L | R | Mean/Waf |
|---|---|---|---|---|---|---|
| 1 | 107.18 | 106.03 | 105.99 | 106.24 | 105.95 | 106.28 |
| 2 | 107.18 | 106.03 | 105.98 | 106.22 | 105.94 | 106.27 |
| 3 | 107.17 | 106.05 | 105.97 | 106.24 | 105.94 | 106.27 |
| 4 | 107.14 | 106.07 | 106.01 | 106.24 | 105.95 | 106.28 |
| 5 | 107.15 | 106.06 | 106.00 | 106.26 | 105.97 | 106.29 |
| 6 | 107.15 | 106.09 | 106.01 | 106.25 | 105.95 | 106.29 |
| 7 | 107.12 | 106.08 | 106.02 | 106.25 | 105.97 | 106.29 |
| 8 | 107.10 | 106.08 | 106.02 | 106.26 | 105.92 | 106.28 |
| 9 | 107.10 | 106.10 | 106.02 | 106.27 | 105.93 | 106.28 |
| 10 | 107.11 | 106.10 | 106.04 | 106.25 | 105.96 | 106.29 |
| 11 | 107.14 | 106.13 | 106.07 | 106.30 | 106.00 | 106.33 |
| 12 | 107.11 | 106.12 | 106.06 | 106.28 | 106.02 | 106.32 |
| 13 | 107.09 | 106.13 | 106.06 | 106.28 | 106.01 | 106.31 |
| 14 | 107.08 | 106.12 | 106.06 | 106.27 | 106.02 | 106.31 |
| 15 | 107.07 | 106.11 | 106.03 | 106.28 | 106.01 | 106.30 |
| Mean | 107.13 | 106.08 | 106.02 | 106.26 | 105.96 | 106.29 |
| Sigma | 0.03 | 0.03 | 0.03 | 0.02 | 0.03 | 0.02 |

The actual measurements were made using an ABSOLUTE ELLIPSOMETER (TM), part of the measurement system of an OPTI-PROBE 5240, manufactured and sold by Therma-Wave. Details of an absolute ellipsometer using a helium neon laser are described in U.S. Pat. No. 5,798,837, incorporated herein by reference in its entirety. The helium neon laser generates a probe beam spot size of about 15 by 30 microns. The beam was scanned in the direction of the wider beam diameter, although scanning can be performed along either of two axes.

The standard deviation (Sigma) for the measurements of each site is shown at the bottom of each Table. Ideally, the thickness measurements at each site would be the same for all the measurements. As can be seen, the average deviation for the measurements using only the site correcting pattern recognition system (Table 1) was 0.37. In contrast, the average deviation for the measurements in Table 2, using the subject line scan system, was only 0.02, an improvement of almost a factor of 20. The only difference between the measurements in Tables 1 and 2 was the use of the scanning algorithm of the present invention in order to determine the data points that would most accurately reflect the true position of the wafer. As can be seen from Table 1, even though a site correcting pattern recognition system was used, a few microns of stage backlash and inaccuracy were enough to substantially degrade performance.

Figure 5:
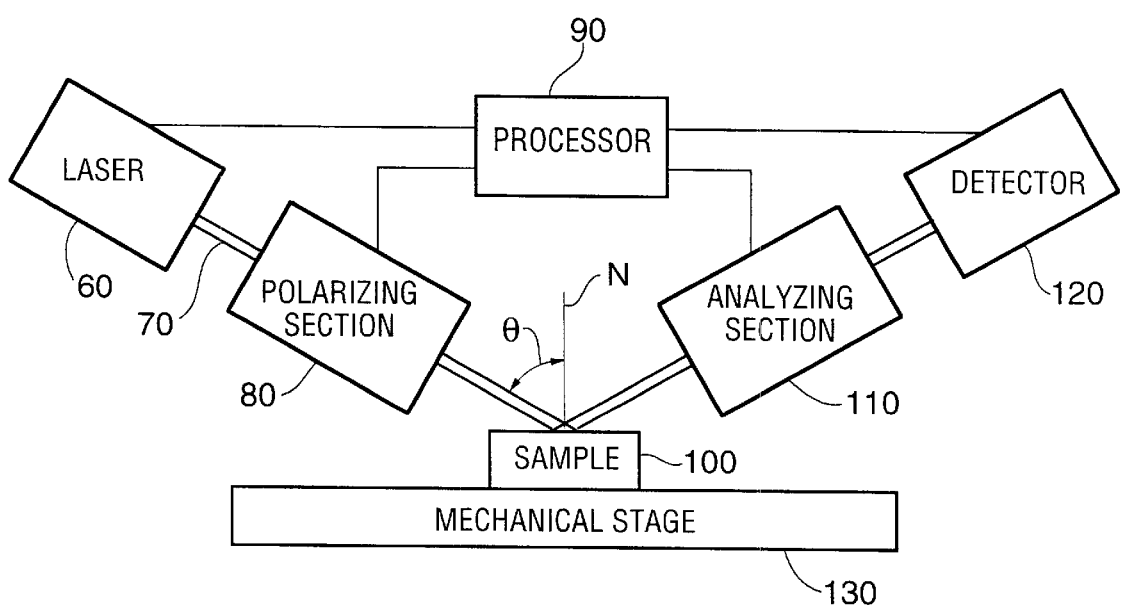
FIG. 5 is a functional diagram of an example of an ellipsometer device that may be used to practice the present invention.

FIG. 5 illustrates a basic form of ellipsometer for evaluating the parameters of a sample 100 in accordance with the present invention. As shown therein, a means, such as laser 60, generates a beam of radiation 70. This beam is passed through a polarizing section 80 for creating a known polarization state of the beam. The beam is then reflected off the sample at an oblique angle of incidence θ with respect to the normal N as shown. The reflected beam is then passed through an analyzing section 110 for isolating the polarization state of the reflected beam. The intensity of the beam is then measured by a photodetector 120. The mechanical stage 130 is used to scan the center of the desired measurement area across the focus of the beam spot in the manner discusses above in order to make a series of measurements. A processor 90 can ultimately be used to determine parameters of the sample 100 by comparing the polarization state of the input beam with the polarization state of the reflected beam.

The scanning technique of the present invention increases both accuracy and repeatability for measurements made on small pads. For still smaller pad sizes the effects of the surrounding material can sometimes not be ignored. In other words, for such pads, even though the scanning method described above may still yield a good repeatability, the accuracy of the measurement even at the center of the pad would be unacceptable. In another aspect of the present invention, we use a novel method of data analysis that allows us to correct for the effects of the surrounding material in analyzing the data. In essence, the data collected at the center of the pad is treated as being created by a superposition of light coming from the pad material itself and light coming from the surrounding material. The influence of the two materials is weighted by the proportion of the light that reflects off the pad as compared with the light that reflects off the surrounding material. In order to estimate these proportions, it is necessary to have knowledge of the optical spot intensity profile, but the profile is something that can be readily determined for the instrument using standard measurement techniques.

Figure 1:
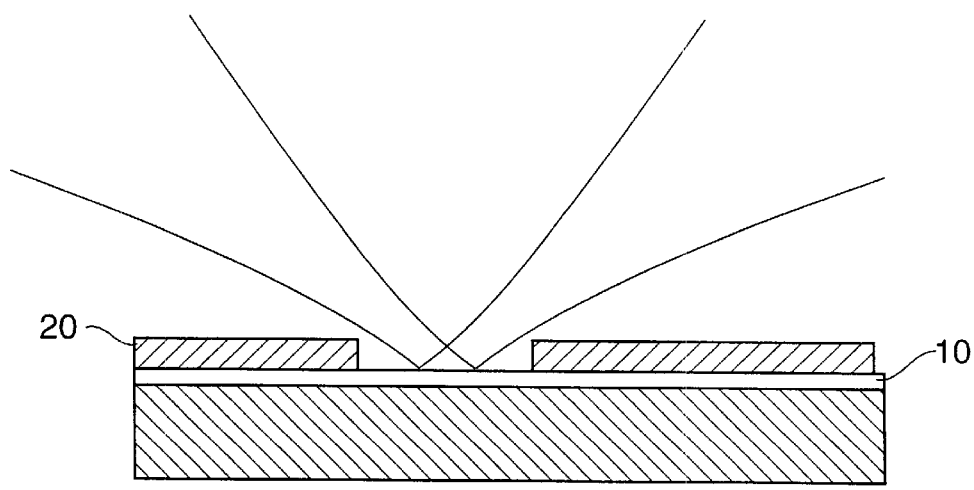
FIG. 1 shows an example of a measurement of a measurement pad comparable in size to the optical spot being used to make the measurement.
Figure 4:
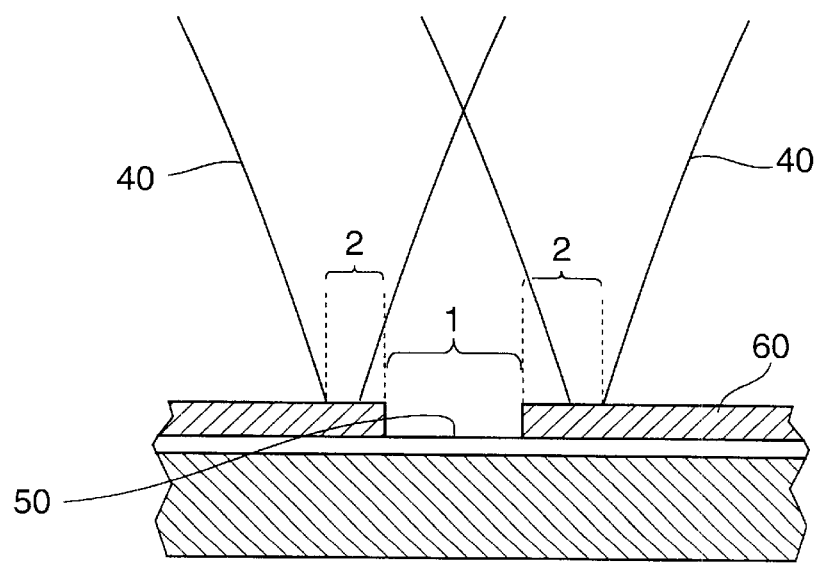
FIG. 4 illustrates the influence of surrounding material on a measurement of a measurement pad comparable in size to the optical spot being used to make the measurement.

For example, and as shown in FIG. 4, the beam spot strikes both the pad 50 and surrounding material 60. Given knowledge of both the dimensions of the pad 50 and the size and profile of the beam spot 40, one can mathematically model the resulting signal to account for both the contribution of the light reflected from the pad 50 (region 1) and the light reflected from the surrounding material 60 (region 2). One approach to this problem is to treat the total reflected signal simply as the superposition of the light signal reflected by the pad region (region 1) and the light signal reflected by the surrounding material (region 2).

Determining each separate contribution from the two regions is a matter of describing the reflection of light by a thin film or stack of thin films. This problem has been treated in detail in *Optical Properties of Thin Film Solids*, O. S. Heavens, Dover edition (1991), pp. 49–92 and *Principles of Optics*, M. Born and E. Wolf, $6^{th}$ (Corrected) edition, pp. 51–70, each of which is hereby incorporated by reference.

Once the reflected field at the lens is known, the intensity of the light at the detector can be determined accordingly based on the optics of the ellipsometric or reflectometric system.

The incoming light may typically be in the form of a laser beam with a Gaussian profile. Since the electric field must satisfy the Maxwell equation, a well focused Gaussian beam may be expressed as follows:

$$E(\vec{x}) = E_0 \int_{k<=k_0} dk e^{-a^2 k^2/4 + i\vec{k}\cdot\vec{r} + i\sqrt{k_0^2 - k^2}z} = E_0 \int dk e^{-(a^2 + i2z/k_0)k^2/4 + i\vec{k}\cdot\vec{r} + ik_0 z}$$

provided that $a >> 1/k_0$. The wave vector k has two dimensional, $k_x$ and $k_y$, where $r=(x,y)$. Carrying out the integration we have the well-known expression describing the propagation of a Gaussian beam, $$E(\vec{x}) = E_0 \frac{1}{a^2 + i2z/k_0} e^{-\frac{r^2}{a^2 + i2z/k_0} + ik_0 z} = E_0 \frac{1}{a^2(z)} e^{-r^2/a^2(z) + ik_0 z}$$

Here $a^2(z)$ is defined by $a^2 + i2z/k_0$ and gives a position-dependent radius of the beam.

We assume that sample is divided into two regions, $x<a$ where the optical reflectivity is $r_1$ and $x \geq a$ where the optical reflectivity is $r_2$. For simplicity, we select our coordinates so that that the incident plane lies in the x-z coordinate system. The system is then uniform in the y direction. We can therefore make a Fourier transformation in the y direction $$\frac{1}{a(z)} e^{-x^2/a^2(z) - k_y^2 a^2(z)/4 - i\left(k_x x - \frac{k_x^2 + k_y^2}{2k_0}z\right)} = \frac{1}{a(z)} e^{-x^2/a^2(z) - k_y^2 a^2(z)/4 - i\left(k_x x - \frac{k_x^2}{2k_0}z\right)}.$$

In the sample plane (after a rotation of angle θ), x→x'=cos θx−sin θz  z→z'=sin θx+cos θz The far field of the optical electric field can be used to predict the intensity of the light at the detector and is expressed as $$\int_{-\infty}^{a} dx e^{-ikx} E(x) r_1 + \int_{a}^{\infty} dx e^{-ikx} E(x) r_2 = r_1 \int dx e^{-ikx} E(x) + (r_2 + r_1) \int_{a}^{\infty} dx e^{-ikx} E(x)$$

The first integral is the field equation for a uniform sample, while the integration in the second term can be written as $$I(k_x, k_y) = E_0 e^{-k_y^2 a^2/4} \int_{a}^{\infty} dx \frac{1}{a(z')} e^{-x'^2/a^2(z') - i\left(k_x x' - \frac{k_x^2}{2k_0}z'\right)}$$

When z=0, we have (excluding the factor containing $k_y$ and $E_0$)

$$I(k_x) = E_0 \frac{1}{\cos\theta} \int_{a\cos\theta}^{\infty} dx \frac{1}{a(\tan\theta x)} e^{-x^2/a^2(\tan\theta x) - i\left(1 - \frac{k_x}{2k_0}\tan\theta\right)k_x x}$$

At normal incidence, the above integration becomes simply $$I = \int_{a}^{\infty} dx e^{-x^2 + ikx} = e^{-a^2 + ika} Wofz(k/2 + ia)$$

Here the function Wofz is the complex error function.

The scope of the present invention is meant to be that set forth in the claims that follow and equivalents thereof, and is not limited to any of the specific embodiments described above.

What is claimed is:

1. An apparatus for evaluating the characteristics of a sample wherein the sample includes a measurement area defined by a region having characteristics different from the surrounding region, comprising:
    a probe beam of radiation which is focused to a spot on the surface of the sample and reflects therefrom and wherein the size of the probe beam spot is similar to the size of the measurement area;
    an optical detector for monitoring the reflected probe beam and generating output signals in response thereto;
    a movable stage for supporting the sample in a manner to translate the sample with respect to the probe beam such that the probe beam spot strikes the sample at a location substantially in the center of the measurement area and at locations on either side thereof allowing optical measurements with the optical detector to be made at a plurality of the locations; and
    a processor for computing the characteristics of the sample for each of the measurement locations and for determining an extremum in the computed characteristics to identify the measurement location best corresponding to the center of the measurement area.

2. An apparatus as recited in claim 1, wherein the stage is initially positioned so that the probe beam spot is located on one side of the measurement area and wherein the stage is linearly translated to cause the probe beam spot to move to the other side of the measurement area while passing over the center of the measurement area.

3. An apparatus as recited in claim 2, wherein the stage is linearly translated along a second axis perpendicular to the first axis so that additional measurements can be made.

4. An apparatus as recited in claim 1, wherein said stage is moved in incremental steps and optical measurements are made in successive positions.

5. An apparatus as recited in claim 1, wherein the extremum is a minimum.

6. An apparatus as recited in claim 1, wherein the extremum is a maximum.

7. An apparatus as recited in claim 1, wherein the optical detector monitors ellipsometric information.

8. An apparatus as recited in claim 1, wherein the optical detector monitors reflectometric information.

* * * * *